US011940435B2

(12) United States Patent
Shi et al.

(10) Patent No.: US 11,940,435 B2
(45) Date of Patent: Mar. 26, 2024

(54) METHOD FOR IDENTIFYING RAW MEAT AND HIGH-QUALITY FAKE MEAT BASED ON GRADUAL LINEAR ARRAY CHANGE OF COMPONENT

(71) Applicant: Jiangsu University, Jiangsu (CN)

(72) Inventors: Jiyong Shi, Jiangsu (CN); Xiaobo Zou, Jiangsu (CN); Yueying Wang, Jiangsu (CN); Xiaowei Huang, Jiangsu (CN); Zhihua Li, Jiangsu (CN); Xinai Zhang, Jiangsu (CN); Di Zhang, Jiangsu (CN)

(73) Assignee: Jiangsu University, Jiangsu (CN)

( * ) Notice: Subject to any disclaimer, the term of this patent is extended or adjusted under 35 U.S.C. 154(b) by 163 days.

(21) Appl. No.: 17/606,053

(22) PCT Filed: Aug. 24, 2021

(86) PCT No.: PCT/CN2021/114199
§ 371 (c)(1),
(2) Date: Oct. 25, 2021

(65) Prior Publication Data
US 2023/0053185 A1  Feb. 16, 2023

(51) Int. Cl.
| | |
|---|---|
| *G06T 7/00* | (2017.01) |
| *G01N 33/12* | (2006.01) |
| *G01J 3/28* | (2006.01) |
| *G01N 1/28* | (2006.01) |
| *G01N 21/359* | (2014.01) |
| *G01N 21/88* | (2006.01) |

(52) U.S. Cl.
CPC .......... *G01N 33/12* (2013.01); *G06T 7/0006* (2013.01); *G01J 3/2823* (2013.01);
(Continued)

(58) Field of Classification Search
CPC ............. G01N 33/12; G01N 21/359; G01N 2001/2893; G01N 2021/8845;
(Continued)

(56) References Cited

U.S. PATENT DOCUMENTS

| 5,595,444 A | * | 1/1997 | Tong | ............... | G01N 33/12 |
| | | | | | 374/45 |
| 2003/0091144 A1 | * | 5/2003 | Bartie | .............. | G01N 23/04 |
| | | | | | 378/53 |

(Continued)

FOREIGN PATENT DOCUMENTS

| CN | 103361422 | 10/2013 |
| CN | 104132896 | 11/2014 |
| CN | 106483221 | 3/2017 |

*Primary Examiner* — Solomon G Bezuayehu
(74) *Attorney, Agent, or Firm* — JCIP GLOBAL INC.

(57) ABSTRACT

The present invention relates to the technical field of identification on adulterated meat, and in particular, to a method for identifying raw meat and high-quality fake meat based on a gradual linear array change of a component. The present invention spatially characterizes changing rules of featured components in the meat with the utilization of sensitivities of the visible/near-infrared spectral signals to changes of the components in the meat and the advantage that spectral scanning can acquire optical signals of the samples spatially and consecutively, further constructs the identification model according to differences in components and spectra of a region of interest in the hyperspectral image by taking a derivative for characterizing rates of change of the featured components.

8 Claims, 2 Drawing Sheets

(52) U.S. Cl.
CPC ... *G01N 2001/2893* (2013.01); *G01N 21/359* (2013.01); *G01N 2021/8845* (2013.01); *G01N 2021/8883* (2013.01); *G06T 2207/30128* (2013.01)

(58) Field of Classification Search
CPC .......... G01N 2021/8883; G06T 7/0006; G06T 2207/30128; G01J 3/2823
See application file for complete search history.

(56) References Cited

U.S. PATENT DOCUMENTS

| | | | |
|---|---|---|---|
| 2008/0064058 A1* | 3/2008 | Kapel | G01N 33/12 435/34 |
| 2008/0204733 A1* | 8/2008 | Jones | G01N 33/12 356/237.1 |
| 2008/0247603 A1* | 10/2008 | Tomic | G01N 33/12 382/110 |
| 2011/0273558 A1* | 11/2011 | Subbiah | G01J 3/2803 348/E7.085 |
| 2011/0293817 A1* | 12/2011 | Hurm | A23L 13/72 426/641 |
| 2015/0296834 A1* | 10/2015 | Geistlinger | A23J 3/14 426/657 |
| 2015/0317803 A1* | 11/2015 | Cooke | G06T 7/0004 382/110 |
| 2018/0310599 A1* | 11/2018 | Ajami | A23L 5/10 |
| 2020/0359637 A1* | 11/2020 | Pein | A22C 17/0073 |
| 2021/0092969 A1* | 4/2021 | Hartwig | G01N 23/04 |
| 2021/0204553 A1* | 7/2021 | Mehta | G06V 20/52 |
| 2021/0315219 A1* | 10/2021 | Peng | A22C 9/004 |

* cited by examiner

IC-1  IC-2  IC-3  IC-4

METHOD FOR IDENTIFYING RAW MEAT AND HIGH-QUALITY FAKE MEAT BASED ON GRADUAL LINEAR ARRAY CHANGE OF COMPONENT

CROSS-REFERENCE TO RELATED APPLICATION

This application is a 371 of international application of PCT application Ser. No. PCT/CN2021/114199, filed on Aug. 24, 2021, which claims the priority benefit of China application no. 202110914828.8, filed on Aug. 10, 2021. The entirety of each of the above mentioned patent applications is hereby incorporated by reference herein and made a part of this specification.

BACKGROUND

Technical Field

The present invention relates to the technical field of identification on adulterated meat, and in particular, to a method for identifying raw meat and high-quality fake meat based on a gradual linear array change of a component.

Description of Related Art

Meat is an important source of high-quality dietary protein and plays an important role in daily diets of consumers. In recent years, while natural and healthy diets are gradually becoming mainstream concepts of the consumers, raw meat from animal carcasses has been more and more popular. The raw meat is highly recognized by the consumers and highly sold because of the special textures and colors as well as the naturally formed internal components and structures. However, with a surge in demand of the consumers on the raw meat, the contradiction between supply and demand is prominent aggressively and high-quality fake meat having the similar appearances and same components with the raw meat is emerging increasingly. Unlike the natural formation of the raw meat, the high-quality fake meat is synthesized artificially by taking minced meat and low value meat as raw materials, imitating the textures and colors of the raw meat and forming blocks with carrageenan and glutamine transaminase or by freezing. Featuring the low cost, and the similar or even same appearances and components with the raw meat, the high-quality fake meat is usually sold by dishonest sellers as the naturally raw meat to affect the consumer rights and the market orders. Hence, there is a need to establish a method for identifying the naturally raw meat and the artificially high-quality fake meat.

The meat is mainly identified from the appearance features and the internal components and there have been the sensory inspection, chromatography, spectrometry and molecular biotechnology. The sensory inspection is mainly intended to identify the adulterated meat from features such as colors, textures, odors and flavors. However, the artificially high-quality fake meat can achieve the same appearance features as the raw meat by dyeing with a food dye, modifying with a food additive and adjusting a placement order, and thus is poorly identified by the sensory inspection. Both the chromatography and the spectrometry (such as patents CN 106483221 A and CN 104132896 A) implement qualitative identification by comparing components in the meat with standard substances. The molecular biotechnology (CN 103361422 A) has the defects of high cost, long time consumption, complicated operation and so on despite the reliable detection result. The above identification methods can only identify different types of adulterated meat, but cannot identify the corresponding high-quality fake meat when the same type of meat is recombined.

The raw meat and the high-quality fake meat are significantly different in formation although both have the similar or even same appearances, components and biological features. The raw meat comes from the naturally growing and developing animal carcasses, with local components changing naturally and gradually from the beginning. The high-quality fake meat of the raw meat is spliced and recombined artificially from the same type of minced meat or low value meat, with components in gaps between the mined meat not changing naturally and gradually, and rates of change of corresponding featured components often greater than those of corresponding components growing naturally. Hence, rates of spatial change of components in meat samples can be used as a basis to identify the raw meat and the high-quality fake meat. In view of this, with the sensitivities of visible/near-infrared hyperspectral signals for contents of components in the meat and spatial distributions thereof, the present invention provides a method for identifying a raw meat and a high-quality fake meat based on a gradual linear array change of a component.

SUMMARY

In view of the defects of the prior art, the present invention provides a method for identifying raw meat and high-quality fake meat based on a gradual linear array change of a component, to identify the raw meat and the high-quality fake meat quickly and accurately.

A method for identifying raw meat and high-quality fake meat based on a gradual linear array change of a component includes construction of an identification model based on a gradual linear array change of a sectional component, and identification of a meat sample to be tested, where step 1: the construction of an identification model based on a gradual linear array change of a sectional component includes the following substeps:

S1: cutting meat longitudinally or transversely to obtain a longitudinal or transverse section of the meat, the meat including raw meat and high-quality fake meat; and specifically providing b raw meat samples and c high-quality fake meat samples, and randomly separating the samples into a calibration set and a prediction set according to a ratio of d:1, b, c and d each being a positive integer;

S2: imaging, by using a visible/near-infrared hyperspectral imaging (HSI) system, the section of the meat processed in S1 to obtain an M*N*W three-dimensional (3D) hyperspectral image, where M and N each represent a number of rows and a number of columns for image pixels at a single wavelength, and W represents a number of wavelengths of the hyperspectral image;

S3: performing independent component analysis (ICA) on the 3D hyperspectral image obtained in S2 and corresponding to the section of the meat to obtain first n independent component images, IC-1, IC-2,. . ., IC-(n-1) and IC-n, corresponding to the hyperspectral image for the section of the meat, where n is a positive integer smaller than or equal to the W;

S4: defining, with a central position of an independent component image IC-i (i$\in$[1, n]) obtained in S3 as a center O-i having a coordinate of (Int(M/2), Int(N/2)), a circular region having a radius of r pixels as a feature extraction region R-i; defining, in the feature extraction region R-i, a polar coordinate system with the O-i as a polar point, a horizontal ray as a polar axis Ox, a pixel as a unit length and a counterclockwise direction as a positive direction, and determining, with the polar coordinate system on the independent component image IC-i, q feature extraction segment endpoints Q-i-j having a coordinate of (r, 360*(j-1)/q), where j∈[1, q]; Int(M/2) represents rounding on M/2, and Int(N/2) represents rounding on N/2; q is an integer greater than 1; and r is a positive integer not greater than min(Int (M/2), Int(N/2)), and M and N each represent a number of rows and a number of columns for the image pixels at the single wavelength;

S5: respectively connecting, with the polar point O-i in the independent component image IC-i in S4 as a start point, the feature extraction segment endpoints Q-i-j by using a line having a width of one pixel to obtain q feature extraction segments OQ-i-j in the independent component image IC-i;

S6: respectively converting an image covered by the q feature extraction segments OQ-i-j in the independent component image IC-i in S5 into a row vector AOQ-i-j; and taking a derivative of the row vector by viewing a pixel intensity in the row vector AOQ-i-j as a function varying with a pixel point to obtain a first-order derivative vector AOQ'-i-j and a second-order derivative vector AOQ''-i-j corresponding to the AOQ-i-j;

S7: counting a gradual linear array change B-i corresponding to the independent component image IC-i with a value a as a determination threshold, where B-i is a number of elements each having an absolute value greater than or equal to the threshold a in the q derivative vectors AOQ'-i-j corresponding to the independent component image IC-i and AOQ''-i-j=0, namely, |AOQ'-i-j|≥a and AOQ''-i-j=0 are met at the same time; and the determination threshold a=|AOQ'-i-j|$_{max}$η, 0<η<1, and |AOQ'-i-j|$_{max}$ being a maximum value in absolute values of elements in the first-order derivative vectors AOQ'-i-j of the q feature extraction segments corresponding to the independent component image IC-i;

S8: establishing a 1\*n matrix C for storing gradual linear array changes B-i (i∈[1, n]) corresponding to the n independent component images, where a gradual linear array change B-i corresponding to an ith independent component image is stored in C(1, i) for construction of the identification model; and a gradual linear array change dataset corresponding to a calibration set in the n independent component images is labeled as C_cal and a gradual linear array change dataset corresponding to a prediction set is labeled as C_pre; and S9: constructing the identification model: constructing, with a reference value 1 as raw meat and a reference value 0 as high-quality fake meat, a reference value dataset Y_cal corresponding to the calibration set and a reference value dataset Y_pre corresponding to the prediction set; constructing the identification model for the raw meat and the high-quality fake meat in combination with the feature dataset C_cal of the calibration set and the feature dataset C_pre of the prediction set in S8; and taking a correct identification rate R of the prediction set as an indicator for measuring performance of the identification model, and labeling a corresponding identification model as Y in response to R≥60%, where $Y=F_{(n,a)(X)}$, X being gradual linear array change datasets corresponding to all independent component images of each sample, n being a positive integer smaller than or equal to W, and a being the determination threshold; and step 2: the identification of a meat sample to be tested includes the following substeps:

S1: acquiring a hyperspectral image corresponding to the meat sample to be tested, and extracting, according to substeps S1 to S8 in step 1, a gradual linear array change dataset C_uk corresponding to the meat sample to be tested; and S2: substituting the C_uk into the identification model $Y=F_{(n,a)(X)}$ in S9 of step 1 to calculate a reference value corresponding to the sample to be tested, where when the reference value predicted by the model is 1, the sample to be tested is the raw meat; and when the reference value predicted by the model is 0, the sample to be tested is the high-quality fake meat, thereby implementing the identification on the meat sample to be tested.

Preferably, the calibration set in S1 includes Int[b*d/(d+1)] raw meat samples and Int[c*d/(d+1)] high-quality fake meat samples in total; and the prediction set includes b-Int[b*d/(d+1)] raw meat samples and c-Int[c*d/(d+1)] high-quality fake meat samples in total, where Int[b*d/(d+1)] and Int[c*d/(d+1)] each represent rounding on b*d/(d+1) and c*d/(d+1).

Preferably, b and c in S1 each are a positive integer greater than 30; and d ranges from 1 to 5.

Preferably, an optimization range for the number n of independent component images in S3 and a step size An thereof are determined by setting a maximum value for the number n of independent component images as $n_{max}$=Int(W*p), p∈[0.5%, 20%], and Int(W*p) representing rounding on W*p; setting a minimum value for the number n of independent component images as $n_{min}$=1, such that the optimization range of the n is $n_{min}n_{max}$; and labeling the step size Δn as f, f being a positive integer.

Preferably, the step size Δn in S3 is 1.

Preferably, an optimization range for the determination threshold a in S7 and a step size Δa thereof are determined by setting the determination threshold a=|AOQ'-i-j|$_{max}$*η, η∈[g%, h%], such that the determination threshold a has a maximum value $a_{max}$=|AOQ'-i-j|$_{max}$*h%, a minimum value $a_{min}$=|AOQ'-i-j|$_{max}$*g%, and the step size Δa=|AOQ'-i-j|$_{max}$*k%, g, h and k each being a positive integer, and g<h.

Preferably, when the correct identification rate R in S9 is a maximum value, a corresponding identification model is labeled as $Y_{op}$, where $Y_{op=F(nnop, aop)}(X)$, and a number of independent component images and a determination threshold corresponding to the model are labeled as optimal number $n_{op}$ of independent component images and an optimal determination threshold $a_{op}$.

Preferably, the identification model for the raw meat and the high-quality fake meat in S9 is established with a k-nearest neighbor (KNN) algorithm.

The symbol * in the above steps has a meaning of multiplication; the letter i in the steps meets i∈[1, n], n being a positive integer smaller than or equal to W; and j∈[1, q], q being an integer greater than 1.

The present invention has the following beneficial effects:

The present invention spatially characterizes changing rules of featured components in the meat with the utilization of sensitivities of the visible/near-infrared spectral signals to changes of the components in the meat and the advantage that spectral scanning can acquire optical signals of the samples spatially and consecutively, and further identifies the raw meat and the high-quality fake meat according to differences in components and spectra of a region of interest (ROI) in the hyperspectral image by taking a derivative for characterizing rates of change of the featured components.

The components in the meat are in a linear relation with the spectral signals, the derivation serves as an important way for characterizing the change trend and the derivative is an indication for the rate of change of the original function. Therefore, even though the high-quality fake meat has the similar colors and components with the raw meat, the technical solutions provided by the present invention can still make an effective distinction according to differences in gradual changes of the featured components in the raw meat which changes naturally and gradually and the high-quality fake meat which is recombined artificially.

DESCRIPTION OF THE EMBODIMENTS

The present invention is further described in detail below with reference to the specific embodiments, but the protection scope of the present invention is not limited thereto.

Embodiment 1

A method for identifying raw meat and high-quality fake meat based on a gradual linear array change of a component includes construction of an identification model based on a gradual change of a sectional component, and identification of a meat sample to be tested.

Step 1: the construction of an identification model based on a gradual change of a sectional component includes the following substeps.

S1: A meat sample is cut longitudinally or transversely to obtain a longitudinal or transverse section of the meat sample, the meat sample including raw meat and high-quality fake meat, and specifically, 80 raw meat samples and 80 high-quality fake meat samples are selected and randomly separated into a calibration set and a prediction set according to a ratio of 3:1, where the calibration set includes 60 raw meat samples and 60 high-quality fake meat samples in total, and the prediction set includes 20 raw meat samples and 20 high-quality fake meat samples in total.

S2: The section of the meat is imaged with a visible/near-infrared HSI system to obtain an 1850*1700*618 3D hyperspectral image, where 1850 and 1700 each represent a number of rows and a number of columns for image pixels at a single wavelength, and 618 represents a number of wavelengths of the hyperspectral image.

S3: ICA is performed on the hyperspectral image obtained in S2 and corresponding to the section of the meat to obtain first n independent component images, IC-1, IC-2,. . ., IC-(n-1) and IC-n, corresponding to the hyperspectral image for the section of the meat.

Figure 1:
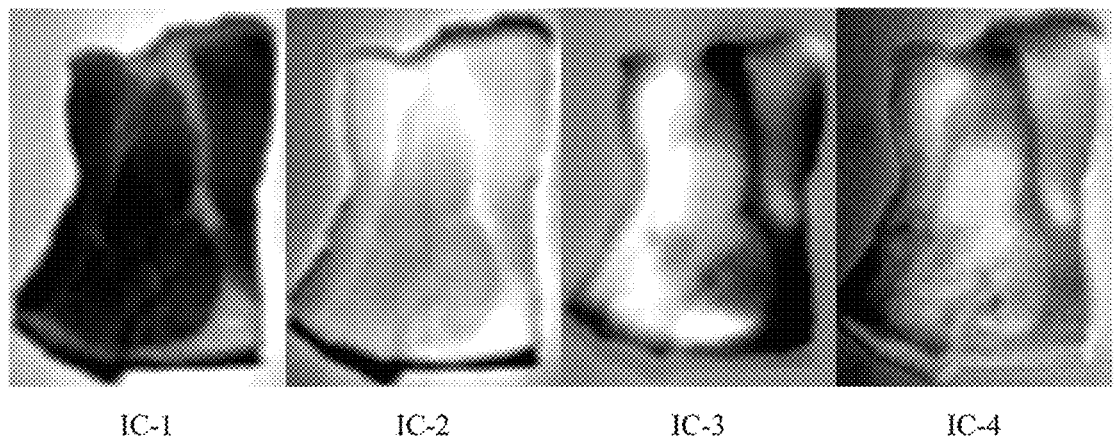
FIG. 1 illustrates a case where a hyperspectral independent component image of a meat sample is respectively IC-1, IC-2, IC-3 and IC-4 when n=4 in Embodiment 1.
Figure 2:
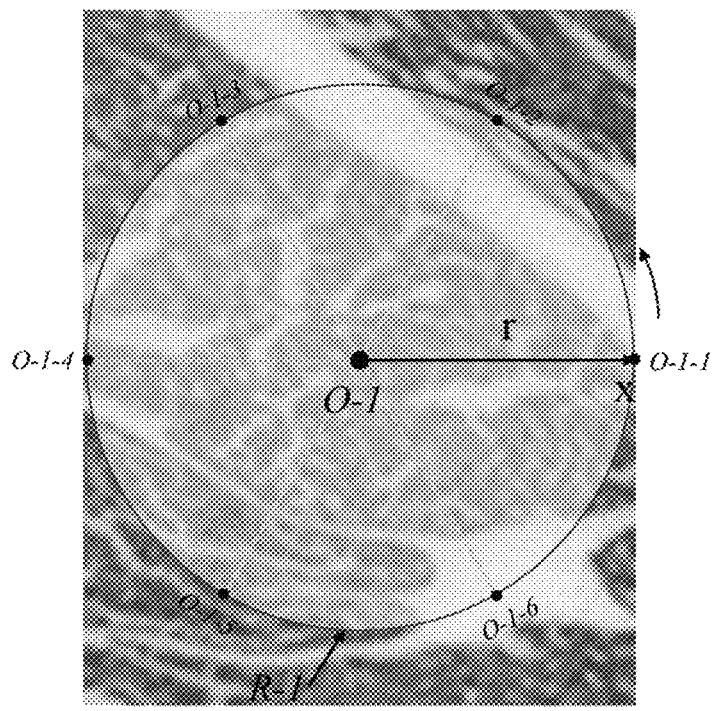
FIG. 2 illustrates a schematic view of a feature extraction segment in an independent component image IC-1 of a meat sample when i=1 and q=6 in Embodiment 1.

An optimization range for the number n of independent component images and a step size Δn thereof are determined as follows. A maximum value for the number n of independent component images is set as $n_{max}$=Int(618*p), p∈[0.5%, 20%], Int(618*p) representing rounding on 618*p, P=0.7%, and $n_{max}$=6. A minimum value for the number n of independent component images is set as $n_{min}$=1, such that the optimization range is 1-6, and with f=1 and the step size Δn=1, the number n of independent component images may be [1, 2, 3, 4, 5, 6]. FIG. 1 illustrates the case where n=4.

S4: With a hyperspectral independent component image IC-1 of the raw meat obtained in S3 as an example and a central position of the IC-1 as a center O-i having a coordinate of (925, 850), a circular region having a radius of 850 pixels is defined as a feature extraction region R-1. A polar coordinate system with the O-1 as a polar point, a horizontal ray as a polar axis Ox, a pixel as a unit length and a counterclockwise direction as a positive direction is defined in the feature extraction region R-1, and six feature extraction segment endpoints Q-1-j (850, 360*(j-1)/6) are determined with the polar coordinate system on the independent component image IC-1, where j∈[1, 6].

Figure 3:
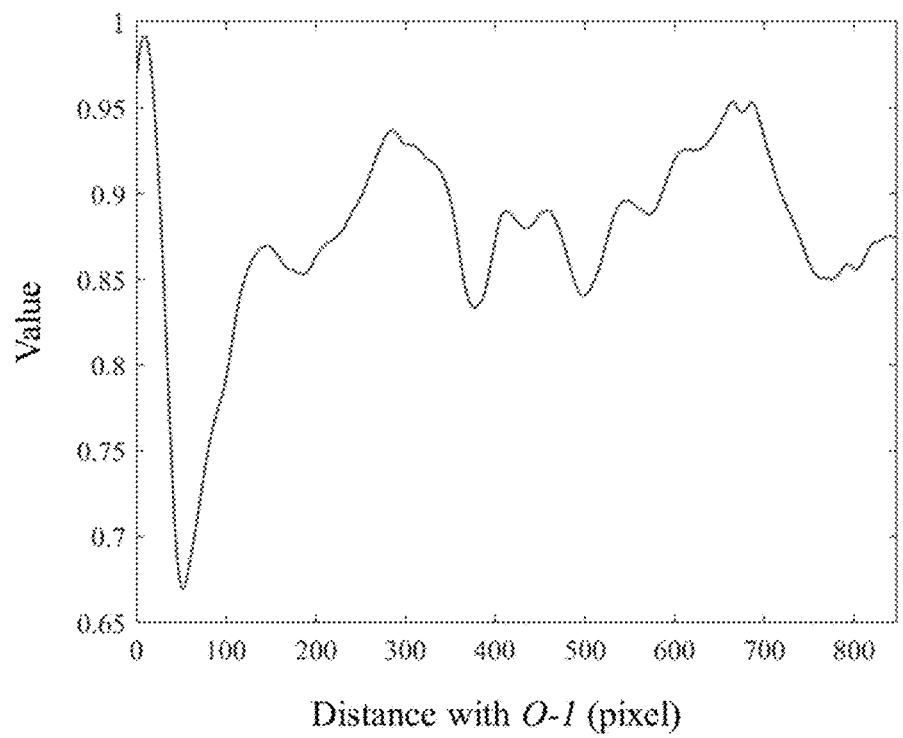
FIG. 3 illustrates a curve corresponding to a row vector AOQ-1-1 of a meat sample OQ-1-1 when i=1 and j=1 in Embodiment 1.

S5: With the polar point O-1 in the independent component image IC-1 as a start point, the feature extraction segment endpoints Q-1-j are respectively connected by using a line having a width of one pixel to obtain six feature extraction segments OQ-1-j, j∈[1, 6], in the independent component image IC-1. FIG. 3 illustrates a schematic view of a feature extraction segment.

Figure 4:
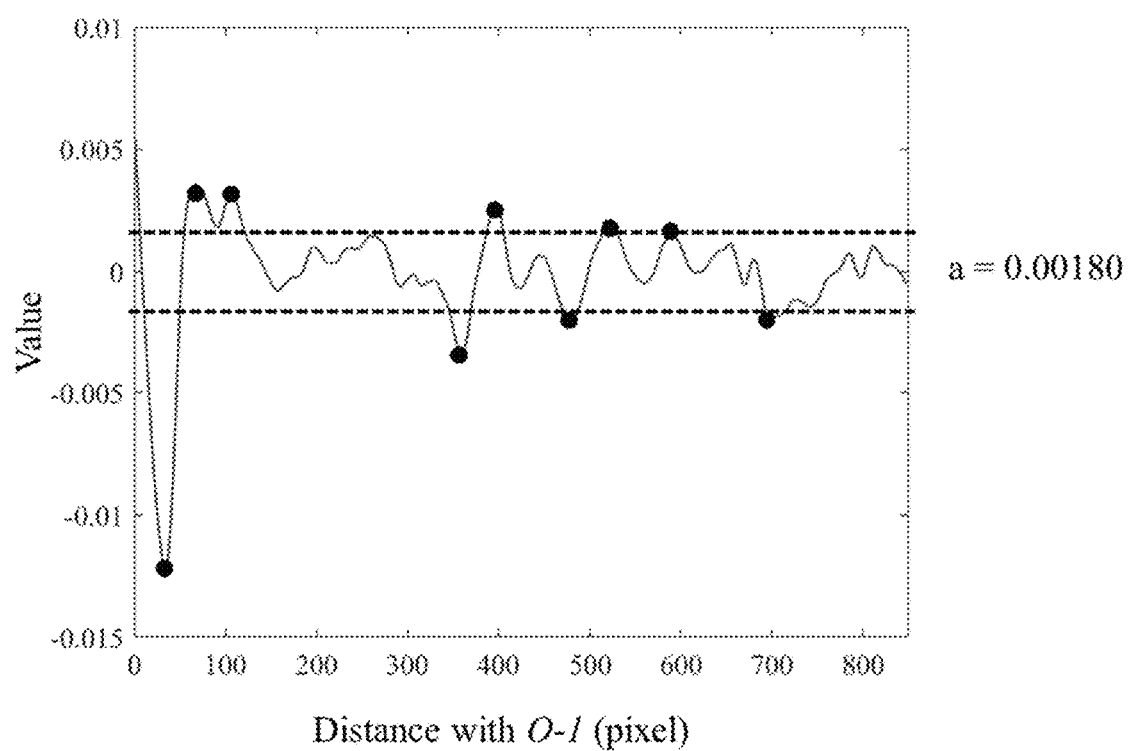
FIG. 4 illustrates a curve corresponding to a first-order derivative vector AOQ'-1-1 of a meat sample OQ-1-1 when i=1 and j=1 in Embodiment 1.

S6: With j=1 as an example, an image covered by a first feature extraction segment OQ-1-1 in the independent component image IC-1 is converted into a row vector AOQ-1-1, and a derivative of the row vector is taken by viewing a pixel intensity in the row vector AOQ-1-1 as a function varying with a pixel point to obtain a first-order derivative vector AOQ'-1-1 and a second-order derivative vector AOQ"-1-1 corresponding to the AOQ-1-1. FIG. 3 illustrates a curve corresponding to a row vector AOQ-1-1 of a meat sample OQ-1-1 when i=1 and j=1, and FIG. 4 illustrates a curve corresponding to a first-order derivative vector AOQ'-1-1 of a meat sample OQ-1-1 when i=1 and j=1.

S7: A gradual linear array change B-1 corresponding to the independent component image IC-1 is counted with a value a as a determination threshold, where B-1 is a number of elements each having an absolute value greater than or equal to the determination threshold a in the six derivative vectors AOQ'-1-j (including AOQ'-1-1, AOQ'-1-2, AOQ'-1-3, AOQ'-1-4, AOQ'-1-5, AOQ'-1-6) corresponding to the independent component image IC-1 and AOQ"-1-1=0. The determination threshold a=|AOQ'-i-j|$_{max}$*η, where 0<η1.

An optimization range of the determination threshold a and a step size Δa thereof are determined as follows. The determination threshold is set as a=|-0.0122|*η, where ∈[5%, 40%], and |-0.0122| is a maximum value in absolute values of elements in first-order derivative vectors AOQ'-i-j of all feature extraction segments corresponding to an independent component image IC-i; and with k=5, the determination threshold a has a maximum value $a_{max}$=0.00488, a minimum value $a_{min}$=0.00061, and a step size Δa of 0.00061, where the determination threshold a may be [0.00061, 0.00122, 0.00183, 0.00244, 0.00305, 0.00366, 0.00427, 0.00488].

S8: A 1*n matrix C for storing gradual linear array changes B-i (i∈[1, n]) corresponding to the n independent component images is established, where the gradual linear array change B-1 corresponding to the first independent component image is stored in C(1, 1) for construction of the identification model; and a gradual linear array change dataset corresponding to a calibration set in the n independent component images is labeled as C_cal and a gradual linear array change dataset corresponding to a prediction set is labeled as C_pre.

S9: The identification model is constructed: With a reference value 1 as raw meat and a reference value 0 as high-quality fake meat, a reference value dataset Y_cal corresponding to the calibration set and a reference value dataset Y_pre corresponding to the prediction set are constructed; the identification model for the raw meat and the high-quality fake meat is constructed based on a KNN algorithm in combination with the feature dataset C_cal of the calibration set and the feature dataset C_pre of the prediction set in S8; and the corresponding identification model is labeled as Y, $Y=F_{(n,a)(X)}$, X being gradual linear array change datasets corresponding to all independent component images of each sample.

With the correct identification rate R of the prediction set as an indicator for measuring performance of the identification model, R≥60% is considered as meeting detection requirements; when the correct identification rate R=98.75% and is the maximum value, a corresponding identification model is the optimal model $Y_{op}$, where $Y_{op=F(4,0.00183)(X)}$, and the number of independent component images and a determination threshold corresponding to the model are an optimal number $n_{op}=4$ of independent component images and an optimal determination threshold $a_{op}=0.00183$.

Step 2: the identification of a meat sample to be tested includes the following substeps:

S1: A hyperspectral image corresponding to the meat sample to be tested is acquired, and according to substeps S1 to S8 in Step 1, a gradual linear array change dataset C_uk corresponding to the meat sample to be tested is extracted.

S2: The C_uk is substituted into the identification model $Y_{op=F(4,0.00183)(X)}$ in S9 of Step 1 to calculate a reference value corresponding to the sample to be tested, where when the reference value predicted by the model is 1, the sample to be tested is the raw meat, and when the reference value predicted by the model is 0, the sample to be tested is the high-quality fake meat, thereby implementing the identification on the meat sample to be tested.

It should be noted that the above embodiments are merely intended to illustrate the present invention, rather than to limit the technical solutions described in the present invention. Therefore, although this specification describes the present invention in detail with reference to the above-mentioned embodiments, the person of ordinary skill in the art should understand that the present invention can still be modified or equivalently replaced. All technical solutions and improvements made without deviating from the spirit and scope of the present invention should fall into the scope of the claims of the present invention.

What is claimed is:

1. A method for identifying raw meat and high-quality fake meat based on a gradual linear array change of a component, specifically comprising the following steps:
   step 1: construction of an identification model based on a gradual linear array change of a sectional component, which comprises the following substeps:
   S1: cutting meat longitudinally or transversely to obtain a longitudinal or transverse section of the meat, the meat comprising raw meat and high-quality fake meat; and specifically providing b raw meat samples and c high-quality fake meat samples, and randomly separating the samples into a calibration set and a prediction set according to a ratio of d:1, b, c and d each are a positive integer;
   S2: imaging, by using a visible or/and near-infrared hyperspectral imaging system, the section of the meat processed in S1 to obtain an M*N*W three-dimensional hyperspectral image, wherein M and N each represent a number of rows and a number of columns for image pixels at a single wavelength, and W represents a number of wavelengths of the hyperspectral image;
   S3: performing independent component analysis on the 3D hyperspectral image obtained in S2 and corresponding to the section of the meat to obtain first n independent component images, IC-1, IC-2, ..., IC-(n-1) and IC-n, corresponding to the hyperspectral image for the section of the meat, wherein n is a positive integer smaller than or equal to the W;
   S4: defining, with a central position of an independent component image IC-i (i∈[1, n]) obtained in S3 as a center O-i having a coordinate of (Int(M/2), Int(N/2)), a circular region having a radius of r pixels as a feature extraction region R-i; defining, in the feature extraction region R-i, a polar coordinate system with the O-i as a polar point, a horizontal ray as a polar axis Ox, a pixel as a unit length and a counterclockwise direction as a positive direction, and determining, with the polar coordinate system on the independent component image IC-i, q feature extraction segment endpoints Q-i-j having a coordinate of (r, 360*(j-1)/q), wherein j∈[1, q]; Int(M/2) represents rounding on M/2, and Int(N/2) represents rounding on N/2; q is an integer greater than 1; and r is a positive integer not greater than min(Int(M/2), Int(N/2));
   S5: respectively connecting, with the polar point O-i in the independent component image IC-i in S4 as a start point, the feature extraction segment endpoints Q-i-j by using a line having a width of one pixel to obtain q feature extraction segments OQ-i-j in the independent component image IC-i;
   S6: respectively converting an image covered by the q feature extraction segments OQ-i-j in the independent component image IC-i in S5 into a row vector AOQ-i-j; and taking a derivative of the row vector by viewing a pixel intensity in the row vector AOQ-i-j as a function varying with a pixel point to obtain a first-order derivative vector AOQ'-i-j and a second-order derivative vector AOQ"-i-j corresponding to the AOQ-i-j;
   S7: counting a gradual linear array change B-i corresponding to the independent component image IC-i with a value a as a determination threshold, wherein B-i is a number of elements each having an absolute value greater than or equal to the threshold a in the q derivative vectors AOQ'-i-j corresponding to the independent component image IC-i and AOQ"-i-j=0, namely, |AOQ'-i-j| ≥a and AOQ"-i-j=0 are met at the same time; and
   the determination threshold $a=|AOQ'\text{-}i\text{-}j|_{max}*\eta$, $0<\eta<1$, and $|AOQ'\text{-}i\text{-}j|_{max}$ is a maximum value in absolute values of elements in the first-order derivative vectors AOQ'-i-j of the q feature extraction segments corresponding to the independent component image IC-i;
   S8: establishing a 1*n matrix C for storing gradual linear array changes B-i (i∈[1, n]) corresponding to the n independent component images, wherein a gradual linear array change B-i corresponding to an ith independent component image is stored in C(1, i) for construction of the identification model; and a gradual linear array change dataset corresponding to a calibration set in the n independent component images is labeled as C_cal and a gradual linear array change dataset corresponding to a prediction set is labeled as C_pre; and
   S9: onstructing the identification model: constructing, with a reference value 1 as raw meat and a reference value 0 as high-quality fake meat, a reference value dataset Y_cal corresponding to the calibration set and a reference value dataset Y_pre corresponding to the prediction set; constructing the identification model for the raw meat and the high-quality fake meat in combination with the feature dataset C_cal of the calibration set and the feature dataset C_pre of the prediction set in S8; and taking a correct identification rate R of the prediction set as an indicator for measuring performance of the identification model, and labeling a corresponding identification model as Yin response to R≥60%, wherein $Y=F(n,a)(X)$, X is gradual linear array change datasets corresponding to all independent component images of each sample, n is a positive integer smaller than or equal to W, and a is the determination threshold; and step 2: identification of a meat sample to be tested, which comprises the following sub steps:

S1: acquiring a hyperspectral image corresponding to the meat sample to be tested, and extracting, according to substeps S1 to S8 in step 1, a gradual linear array change dataset C_uk corresponding to the meat sample to be tested; and S2: substituting the C_uk into the identification model $Y=F(n,a)(X)$ in S9 of step 1 to calculate a reference value corresponding to the sample to be tested, wherein when the reference value predicted by the model is 1, the sample to be tested is the raw meat; and when the reference value predicted by the model is 0, the sample to be tested is the high-quality fake meat, thereby implementing the identification on the meat sample to be tested.

2. The method for identifying the raw meat and the high-quality fake meat based on the gradual linear array change of the component according to claim 1, wherein the calibration set in S1 comprises Int[b*d/(d+1)] raw meat samples and Int[c*d/(d+1)] high-quality fake meat samples in total; and the prediction set comprises b-Int[b*d/(d+1)] raw meat samples and c-Int[c*d/(d+1)] high-quality fake meat samples in total, wherein Int[b*d/(d+1)] and Int[c*d/(d+1)] each represent rounding on b*d/(d+1) and c*d/(d+1).

3. The method for identifying the raw meat and the high-quality fake meat based on the gradual linear array change of the component according to claim 1, wherein b and c in S1 each are a positive integer greater than 30; and d ranges from 1 to 5.

4. The method for identifying the raw meat and the high-quality fake meat based on the gradual linear array change of the component according to claim 1, wherein an optimization range for the number n of independent component images in S3 and a step size Δn thereof are determined by setting a maximum value for the number n of independent component images as $n_{max}=Int(W*p)$, $p\in[0.5\%, 20\%]$, and Int(W*p) representing rounding on W*p; setting a minimum value for the number n of independent component images as $n_{min}=1$, such that the optimization range of the n is $n_{min}$-$n_{max}$; and labeling the step size Δn as f, f is a positive integer.

5. The method for identifying the raw meat and the high-quality fake meat based on the gradual linear array change of the component according to claim 4, wherein the step size Δn in S3 is 1.

6. The method for identifying the raw meat and the high-quality fake meat based on the gradual linear array change of the component according to claim 1, wherein an optimization range for the determination threshold a in S7 and a step size Δa thereof are determined by setting the determination threshold $a=|AOQ'-i-j|_{max}*\eta$, $\eta\in[g\%, h\%]$, such that the determination threshold a has a maximum value $a_{max}=|AOQ'-i-j|_{max}*h\%$, a minimum value $a_{min}=|AOQ'-i-j|_{max}*g\%$, and the step size $\Delta a=|AOQ'-i-j|_{max}*k\%$, g, h and k each are a positive integer, and g<h.

7. The method for identifying the raw meat and the high-quality fake meat based on the gradual linear array change of the component according to claim 1, wherein when the correct identification rate R in S9 is a maximum value, a corresponding identification model is labeled as $Y_{op}$, where $Y_{op}=F_{nop,aop}(X)$, and a number of independent component images and a determination threshold corresponding to the model are labeled as an optimal number $n_{op}$ of independent component images and an optimal determination threshold $a_{op}$.

8. The method for identifying the raw meat and the high-quality fake meat based on the gradual linear array change of the component according to claim 1, wherein the identification model for the raw meat and the high-quality fake meat in S9 is established with a k-nearest neighbor (KNN) algorithm.

* * * * *

UNITED STATES PATENT AND TRADEMARK OFFICE
CERTIFICATE OF CORRECTION

| | | |
|---|---|---|
| PATENT NO. | : 11,940,435 B2 | Page 1 of 1 |
| APPLICATION NO. | : 17/606053 | |
| DATED | : March 26, 2024 | |
| INVENTOR(S) | : Jiyong Shi et al. | |

It is certified that error appears in the above-identified patent and that said Letters Patent is hereby corrected as shown below:

On the Title Page

Item (30) Foreign Application Priority Data Should read: Aug. 10, 2021 (CN) ...202110914828.8

Signed and Sealed this
Eleventh Day of June, 2024

Katherine Kelly Vidal
*Director of the United States Patent and Trademark Office*